United States Patent [19]

Sykes et al.

[11] 4,405,716

[45] Sep. 20, 1983

[54] PROCESS FOR PREPARING 1-CARBA-2-PENEM-3-CARBOXYLIC ACID

[75] Inventors: Richard B. Sykes, Belle Mead; Jerry S. Wells, Ringoes, both of N.J.

[73] Assignee: E. R. Squibb & Sons, Inc., Princeton, N.J.

[21] Appl. No.: 371,087

[22] Filed: Apr. 23, 1982

[51] Int. Cl.³ .................. C12P 17/18; C12P 17/10; C12P 7/40; C12R 1/18

[52] U.S. Cl. .................. 435/119; 435/121; 435/136; 435/847

[58] Field of Search .......... 435/119, 121, 136, 847

[56] References Cited

U.S. PATENT DOCUMENTS 4,207,395 6/1980 Cassidy et al. ................ 435/119
4,247,640 1/1981 Kempf et al. ................ 435/119

OTHER PUBLICATIONS

Journ. Amer. Chem. Soc., 100, pp. 8006–8007 (1978).
Journ. Antibiotics, 34, pp. 1224–1226 (1981).

*Primary Examiner*—Thomas G. Wiseman
*Assistant Examiner*—Deborah A. Grossman
*Attorney, Agent, or Firm*—Lawrence S. Levinson; Donald J. Barrack

[57] ABSTRACT

Culturing aerobically *Erwinia carotovora* SC 12,637 A.T.C.C. No. 39048 or *Erwinia herbicola* SC 12,638 A.T.C.C. No. 39049 in a culture medium containing assimilable carbon and nitrogen sources yields 1-carba-2-penem-3-carboxylic acid.

4 Claims, No Drawings

PROCESS FOR PREPARING 1-CARBA-2-PENEM-3-CARBOXYLIC ACID

RELATED APPLICATION

U.S. patent application Ser. No. 332,056, filed Dec. 18, 1981, now U.S. Pat. No. 4,362,814, issued Dec. 7, 1982, discloses that aerobically culturing Serratia sp. SC 11,482 A.T.C.C. No. 39006 in a culture medium containing assimilable carbon and nitrogen sources yields 1-carba-2-penem-3-carboxylic acid.

BACKGROUND OF THE INVENTION

The antibiotic 1-carba-2-penem-3-carboxylic acid is reported by Cama and Christensen in JACS, 100, 8006 (1978). 1-Carba-2-penem-3-carboxylic acid is prepared chemically.

1-Carba-2-penem-3-carboxylic acid, p-nitrobenzyl ester can be prepared from the corresponding free acid and can be used to prepare various 2-substituted-1-carba-2-penem-3-carboxylic acids which have antibacterial activity; see Basker, et al., *J. Antibiotics,* 34:1224 (1981).

SUMMARY OF THE INVENTION

The antibiotic 1-carba-2-penem-3-carboxylic acid (systematic name: 7-oxo-1-azabicyclo [3.2.0]hept-2-ene-2-carboxylic acid), i.e.,

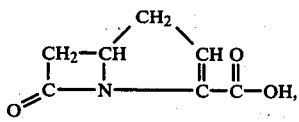

can be produced by culturing aerobically *Erwinia carotovora* SC 12,637 or *Erwinia herbicola* SC 12,638 in a culture medium containing carbon and nitrogen sources until 1-carba-2-penem-3-carboxylic acid is accumulated and then recovering the antibiotic from the medium.

DETAILED DESCRIPTION OF THE INVENTION

The microorganisms used in the present invention are strains belonging to the genus Erwinia that are isolated from plants and soil. The strain designated as *Erwinia carotovora* SC 12,637, has been deposited as No. 39048 in the permanent collection of the American Type Culture Collection, Rockville, Md. The strain designated as *Erwinia herbicola* SC 12,638 has been deposited as No. 39049 in the permanent collection of the American Type Culture Collection, Rockville, Md. A sample of each microorganism can be obtained from that institution. In addition to the specific microorganisms described herein, it should be understood that mutants of the microorganisms (e.g., mutants produced through the use of X-rays, ultraviolet radiation or nitrogen mustards) can also be cultured to produce 1-carba-2-penem-3-carboxylic acid.

*Erwinia carotovora* SC 12,637 A.T.C.C. No. 39048 and *Erwinia herbicola* SC 12,638 A.T.C.C. No. 39049 are fermentative gram-negative peritrichous flagellated rods. The assignment of group for these microorganisms was made on the basis of the biochemical properties listed in the following table.

| Character | A.T.C.C. No. 39048 | A.T.C.C. No. 39049 |
|---|---|---|
| Cytochrome oxidase | − | − |
| [1]Pectinolytic | +++ | − |
| Gelatinase | + | − |
| Gluconate | − | + |
| DNase | − | − |
| Chitinase | NT | − |
| Pigment | − | Yellow |
| Aesculin hydrolysis | + | − |

[1]Determined on a mixed salts-yeast extract pection medium
Legend:
+ = positive for character
− = negative for character
+++ = strongly positive for character
NT = not tested

*Erwinia carotovara* SC 12,637 A.T.C.C. No. 39048 and *Erwinia herbicola* SC 12,638 A.T.C.C. No. 39049 were isolated from plant samples containing the bacteria by placing approximately 1 gram of the plant root or stem sample in 100 ml of sterile saline, mixing and then preparing a series of dilutions in sterile saline. Dilutions were then spread-plated onto the following agar media in order to obtain isolated colonies:

| | | Grams |
|---|---|---|
| (1) | Yeast Extract | 5.0 |
| | Glucose | 10.0 |
| | Crude Agar | 12.5 |
| | Plant Extract | 400 |
| | Distilled Water | 600 |
| (2) | Yeast Extract | 5.0 |
| | Glucose | 10.0 |
| | Agar | 17.5 |
| | Compost Extract | 400 |
| | Tap Water | 600 |
| (3) | Glycerol | 20.0 |
| | Glycine | 2. |
| | NaCl | 1. |
| | K$_2$HPO$_4$ | 1. |
| | FeSO$_4$.7 H$_2$O | 0. |
| | MgSO$_4$.7 H$_2$O | 0. |
| | CaCO$_3$ | 0. |
| | Distilled water to 1 liter | |
| | pH adjusted to 7.0 | |

The media were autoclaved at 121° C. for 30 minutes.

Fermentation of the Microorganisms and Determination of the Antibiotic

The antibiotic 1-carba-2-penem-3-carboxylic acid is produced by cultivating *Erwinia carotovora* SC 12,637 A.T.C.C. No. 39048 or *Erwinia herbicola* SC 12,638 A.T.C.C. No. 39049 at, or near, room temperature (about 25° C.) under submerged aerobic conditions in an aqueous nutrient medium containing an assimilable carbohydrate and nitrogen source. The fermentation is carried out for about 18 hours.

The following is a detailed description of the fermentation of *Erwinia carotovora* SC 12,637 A.T.C.C. No. 39048 and *Erwinia herbicola* SC 12,638 A.T.C.C. No. 39049 and the isolation of the resulting antibiotic.

FLASK FERMENTATION

*Erwinia carotovora* SC 12,637 A.T.C.C. No. 39048 and *Erwinia herbicola* SC 12,638 A.T.C.C. No. 39049 were maintained on the following sterilized medium (A):

| | Grams |
|---|---|
| Yeast Extract | 1 |
| Beef Extract | 1 |
| NZ Amine-A | 2 |
| Glucose | 10 |
| Agar | 15 |

Distilled H₂O to 1 liter
Adjust pH to 7.3 before sterilization of 121° C. for 30 minutes.

A loopful of surface growth from an agar slant (medium A) of *Erwinia carotovora* SC 12,637 A.T.C.C. No. 39048 or *Erwinia herbicola* SC 12,638 A.T.C.C. No. 39049 was used to inoculate 250 ml Erlenmeyer flasks containing 50 ml of Antibiotic Assay Broth (AAB), (Baltimore Biological Laboratory, Cockeysville, Md.).

After inoculation, the flasks were then incubated at 25° C. on a rotary shaker (300 rpm; 2-inch stroke) for approximately 24 hours. After the appropriate incubation, as described above, 1% (vol/vol) transfers were made from the grown culture flasks to 250 ml Erlenmeyer flasks each containing 50 ml of sterilized AAB medium.

After inoculation, the flasks were incubated at 25° C. on a rotary shaker (300 rpm; 2-inch stroke) for approximately 18–22 hours. At this time the broths were centrifuged to remove the cells and the supernatant broths were retained for testing.

Determination of the Antibiotic

To ascertain that the above-prepared fermentation broths did in fact contain 1-carba-2-penem-3-carboxylic acid, the activities of the fermentation broths were compared with the activity of a fermentation broth (prepared as described in U.S. patent application Ser. No. 332,056, filed Dec. 18, 1981, now U.S. Pat. No. 4,362,814, issued Dec. 7, 1982, by culturing Serratia sp. SC 11,482 A.T.C.C. No. 39006) known to contain 1-carba-2-penem-3-carboxylic acid. The results of the comparison are reported below, and do show that the fermentation broths prepared above contain 1-carba-2-penem-3-carboxylic acid.

| Conditions | Activities of Fermantation Broth Filtrates | | |
|---|---|---|---|
| | *Erwinia Corotovora* | *Erwinia herbicola* | Serratia sp. SC 11,482 |
| Zone Sizes (mm): | | | |
| (1) *Bacillus licheniformis* SC 9262 | 15–18 | 15–18 | 22–24 |
| (2) *Enterobacter aerogenes* SC 12,535 | 20–22 | 20–22 | 22–24 |
| (3) *Escherichia coli* JD41 | — | — | — |
| (4) Differential Activity vs. *E. coli* SC 12,155 and *E. coli* SC 2927 | 28–30/- | 28–30/- | 30–33/- |
| Spheroplasts and/or Morphological Abnormalities: | | | |
| *Proetus mirabilis* SC 3855 | + (within 1.5 hrs.) | + (within 1.5 hrs.) | ++ (within 1.5 hrs.) |
| Thin-Layer Chromatography: | | | |
| S&S Cellulose CH₃CN:H₂O (3:1) (3:2) | .1 streaking | .1 streaking | .1 streaking |
| High Voltage Electrophoresis 2,000 Volts, 30 Minutes: (Mobility Relative to Na Nosylate) | | | |
| pH 7.0 | .95 | .95 | .95 |
| pH 2.0 | material destroyed | material destroyed | material destroyed |
| Staphylococcus Lactamase Stability | unstable | unstable | unstable |
| pH Stability (Overnight) | | | |
| pH 7.0 | stable | stable | stable |
| pH 2.0 | unstable | unstable | unstable |

Isolation of the Antibiotic

The antibiotic can be adsorbed from the broth supernate onto charcoal and can be stored in this form at −90° C. for extended periods with substantial loss of activity. Elution from the charcoal with acetone-water (7:3) gives a concentrate that can be further purified by ion-exchange chromatography on Dowex 1- X8 resin (styrene-divinylbenzene copolymer gel resin with $CH_2N^+(CH_3)_3$ groups attached, Dow Chemical Company).

What is claimed is:

1. A process for the preparation of 1-carba-2-penem-3-carboxylic acid which comprises culturing aerobically *Erwinia carotovora* SC 12,637 A.T.C.C. No. 39048 or *Erwinia herbicola* SC 12,638 A.T.C.C. No. 39049 in a culture medium containing assimilable carbon and nitrogen sources until 1-carba-2-penem-3-carboxylic acid is accumulated, and then recovering the 1-carba-2-penem-3-carboxylic acid from the medium.

2. A process in accordance with claim 1 wherein *Erwinia carotovora* SC 12,637 A.T.C.C. No. 39048 is cultured.

3. A process in accordance with claim 1 wherein *Erwinia herbicola* A.T.C.C. No. 39049 is cultured.

4. A process in accordance with claim 1 wherein the culturing is carried out at about 25° C.

* * * * *